United States Patent
Schmitt

(10) Patent No.: US 7,110,507 B2
(45) Date of Patent: Sep. 19, 2006

(54) APPARATUS FOR RADIATION IMAGE RECORDING

(75) Inventor: Thomas Schmitt, Forchheim (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 10/997,959

(22) Filed: Nov. 29, 2004

(65) Prior Publication Data

US 2005/0190888 A1 Sep. 1, 2005

(30) Foreign Application Priority Data

Nov. 28, 2003 (DE) ............... 103 55 616

(51) Int. Cl.
*G21K 1/00* (2006.01)
(52) U.S. Cl. .................................. 378/154
(58) Field of Classification Search ........ 378/154, 378/155, 186
See application file for complete search history.

(56) References Cited

U.S. PATENT DOCUMENTS 4,602,157 A  7/1986 Kayser .............. 250/590
6,181,773 B1 * 1/2001 Lee et al. .............. 378/155
6,282,264 B1  8/2001 Smith et al. .............. 378/189

FOREIGN PATENT DOCUMENTS

DE  101 47 949 A1  4/2003

* cited by examiner

*Primary Examiner*—Courtney Thomas
(74) *Attorney, Agent, or Firm*—Harness, Dickey & Pierce, P.L.C.

(57) ABSTRACT

An apparatus for radiation image recording includes a radiation receiver to which radiation can be applied and which converts the incident radiation to an electrical charge which represents a measure of the incident radiation and which can be read line-by-line via a reading device. It further includes a scattered beam grid, which is associated with the radiation receiver and which includes absorption elements which run in straight lines. The absorption elements are arranged at an angle to the line-by-line reading direction.

18 Claims, 1 Drawing Sheet

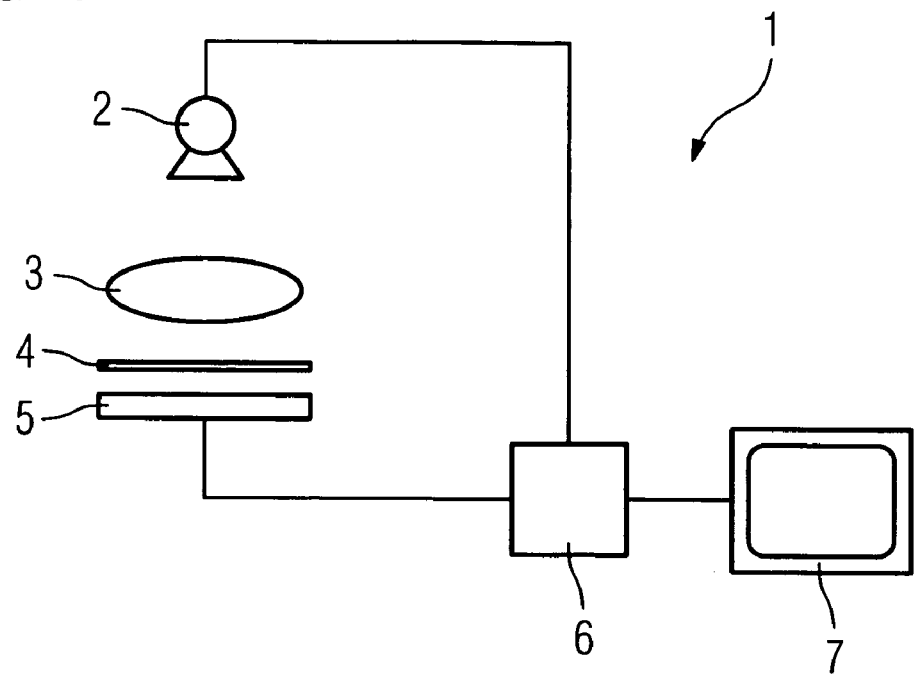
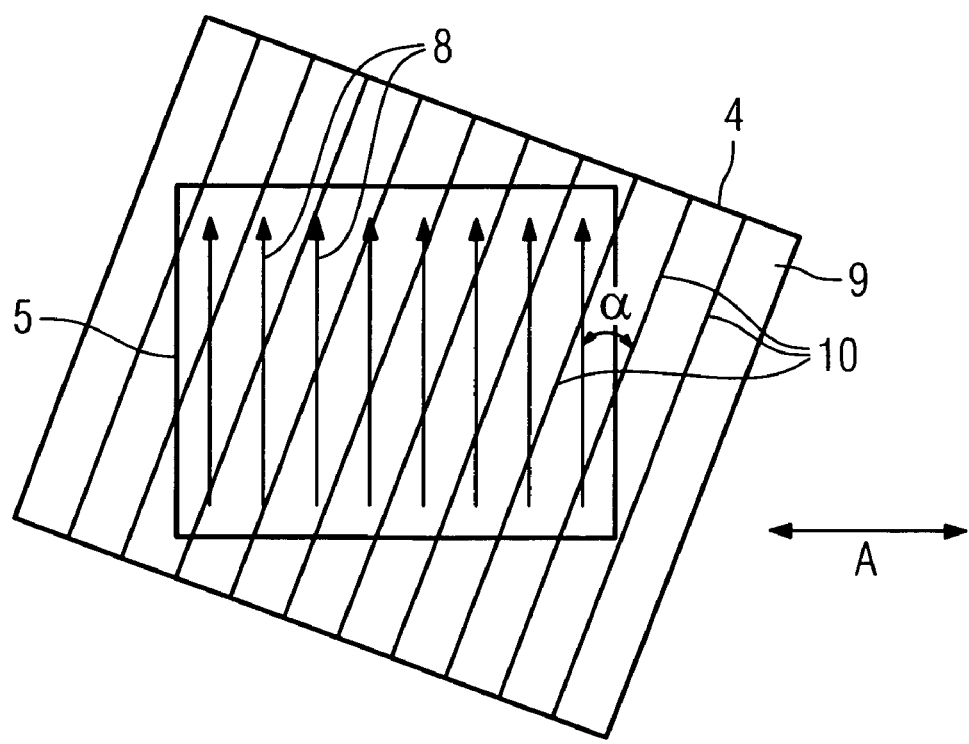

APPARATUS FOR RADIATION IMAGE RECORDING

The present application hereby claims priority under 35 U.S.C. §119 on German patent application number DE 103 55 616.8 filed Nov. 28, 2003, the entire contents of which are hereby incorporated herein by reference.

FIELD OF THE INVENTION

The invention generally relates to an apparatus for radiation image recording. Preferably, it relates to one including a radiation receiver to which radiation can be applied and which converts the incident radiation to an electrical charge which represents a measure of the incident radiation and which can be read line-by-line via a reading device.

BACKGROUND OF THE INVENTION

Apparatuses such as these are known, for example, as X-ray recording devices. The radiation which is emitted from the X-ray source passes through the examination object and strikes the radiation receiver, which converts the radiation that is incident there to a local electrical charge. This charge represents a measure of the locally incident radiation. This electrical charge can be read line-by-line, that is to say in a defined reading direction, via a reading device. The signals which are detected and produced in the process are then processed to form a radiation image, which can be output on a monitor.

The radiation which is passed through the object can be distinguished by two radiation components. Firstly the primary radiation, which strikes the radiation receiver without being scattered by the object, and secondly the secondary radiation, referred to as scattered radiation, which is scattered in the object and then strikes the radiation receiver with a scattered incidence direction. This scattered radiation is disadvantageous, since it makes the image quality poorer.

It is known for scattered beam grids to be used in order to reduce the scattered radiation, and these grids are connected immediately upstream of the radiation receiver. A scattered beam grid of a normal type comprises a large number of linear absorption elements which are incorporated in a carrier material, as a rule thin lead absorption laminates, which absorb the scattered radiation. Thus, while the primary radiation passes through the scattered beam grid essentially without any impediment, the majority of the secondary radiation is absorbed by the scattered beam grid.

However, one disadvantage is the fact that the regularity of the arrangement of the absorption elements, which all run parallel to one another, and the fact that the stored charge is likewise read in a geometrically standard form, specifically line-by-line, makes it possible for so-called Moiré effects to occur. This is an interference phenomenon which has a disadvantageous effect on the quality of the radiation image that is produced.

U.S. Pat. No. 6,282,264 B1 relates to a digital, two-dimensional X-ray detector which can be moved to different positions in order to allow different X-ray protocols to be carried out. The system for positioning the digital detector comprises a detector which in turn comprises a digital X-ray detector arrangement and a scattered beam grid.

DE 101 47 949 A1 discloses a method for production and fitting of a collimator to a Gamma detector for nuclear medicine.

U.S. Pat. No. 4,602,157 describes a device for production of X-ray records, in which a storage film is used as a radiation receiver for the production of X-ray records.

SUMMARY OF THE INVENTION

An embodiment of the invention is based on a problem of specifying an apparatus which offers the capability to reduce Moiré effects in a radiation image recording apparatus having a radiation receiver which can be read line-by-line and having a line scattered beam grid.

In order to solve this problem for an apparatus, an embodiment of the invention provides for the absorption elements to be positioned at an angle to the line-by-line reading direction.

While, in the case of known apparatuses, the absorption elements, which run in straight lines, are parallel to the reading direction, an embodiment of the invention provides the absorption elements to be effectively twisted with respect to the reading direction so that they are at an angle to the reading direction, that is to say they are no longer parallel to it. This is because it has been found that one reason for the occurrence of Moiré effects is the parallelity between the absorption elements and the reading direction.

If the two are now rotated with respect to one another according to an embodiment of the invention, then the formation of Moiré effects can be reduced as a result of the irregularity that this results in. This effect can be achieved with any desired scattered beam grids, that is to say even when using multiple line grids with a very large number of lines per square centimeter, as well as focused or unfocused grids.

The angle through which the two apparatus elements must be rotated with respect to one another should, according to an embodiment of the invention, be $\geq 5°$ and $\leq 90°$.

The grid itself can expediently be moved with respect to the radiation receiver. Thus, the grid is moved backwards and forwards continuously while recording the radiation image, and this serves to further reduce Moiré effects.

According to a first embodiment invention alternative, the scattered beam grid can be arranged such that it is rotated with respect to the fixed-position radiation receiver. In this embodiment, the radiation receiver remains in a defined position with respect to the apparatus, that is to say it is not changed from its previous arrangement. In fact, the scattered beam grid is moved to a new position, in which the angled geometry according to the invention is assumed. In this case, it is expedient for the grid to be designed such that it can be inserted into a conventional grid drawer, and when in the inserted position is rotated with respect to the radiation receiver.

This refinement according to an embodiment of the invention makes it possible to use the conventional grid drawer mechanical system, that is to say to use known grid drawers, without, for example, having to modify the scattered beam grid recording or the guide mechanisms etc. there. Furthermore, this also makes it possible to convert already existing apparatuses, after which no design changes need be carried out.

As an alternative to the embodiment with an unchanged radiation receiver and a newly positioned grid, the configuration can also be reversed. Thus, the radiation receiver may be arranged rotated with respect to the fixed-position scattered beam grid. For example, it is feasible to mount the radiation receiver such that it can itself be rotated about a axis at right angles to the scattered beam grid plane, in order in this way to produce the angled arrangement according to an embodiment of the invention. In addition, it is possible to design the grid drawer such that it can be rotated or to accommodate the scattered beam grid itself in the grid drawer such that it can be rotated.

By way of example, a digital solid-state detector may be used as the radiation receiver for the apparatus according to an embodiment of the invention, in which a pixel matrix is provided which is read line-by-line by means of associated reading electronics. Alternatively, a storage film can also be used as the radiation receiver, which is read in a separate reading device.

BRIEF DESCRIPTION OF THE DRAWINGS

Further advantages, features and details of the invention will become evident from the exemplary embodiment which is described in the following text, and from the drawings, in which:

FIG. 1 shows an outline sketch of an apparatus according to an embodiment of the invention, and FIG. 2 shows an outline sketch of the arrangement of the scattered beam grid with respect to the radiation receiver.

DETAILED DESCRIPTION OF THE EXEMPLARY EMBODIMENTS

FIG. 1 shows an outline sketch of an apparatus 1 according to an embodiment of the invention, including a radiation source 2 via which radiation can be emitted and can be supplied to an object 3. The radiation which passes through the object 3 strikes a scattered beam grid 4, which is followed by a radiation detector 5, in the illustrated example a solid-state radiation detector, by way of example. The operation of the radiation source 2 and of the radiation receiver 5 is controlled by a central control device 6, including the reading operation of the radiation receiver in which the radiation causes electrical charge to be released locally and to be generated as a function of the extent of the locally incident radiation. In a digital solid-state detector, the charge, which is generated on a pixel basis, is read pixel-by-pixel and line-by-line by associated reading electronics. The signals which are produced in this case are passed to the control device 6, which processes them and produces a radiation image, which can be output on a monitor 7.

FIG. 2 shows an enlarged illustration of the arrangement of the scattered beam grid 4 with respect to the radiation receiver 5. As described, the radiation receiver 5 has a pixel matrix which is read line-by-line. The arrows 8 illustrate an example of the reading direction.

The scattered beam grid 4 includes a carrier 9 in which a large number of linear absorption laminates 10 which run in straight lines are integrated. These may either run completely parallel to one another, as is the case with an unfocused beam grid. However, they may also be tilted somewhat with respect to one another towards the edges, so that the scattered beam grid is focused with respect to the focus of the radiation source 2.

In any case, it can be seen that the reading direction, represented by the arrows 8, and the absorption elements 10 are at an angle α to one another. The scattered beam grid 4 is, as can be seen, arranged rotated with respect to the solid-state detector 5. The misalignment between the reading direction and the direction of the absorption element, that is to say the fact that they no longer run parallel to one another, makes it possible to reduce the occurrence of Moiré effects.

A further contribution to this is the fact that the scattered beam grid 4 can be moved with respect to the radiation receiver 5, as is indicated by the double-headed arrow A, and this is also expediently controlled via the control device 6. The scattered beam grid 4 is in this case moved in a direction at right angles to the reading direction, as indicated by the arrows 8. However, it would also be feasible to move the scattered beam grid in a direction at right angles to the direction of the absorption elements 10. However, it is not necessary for the grid to be moveable, and a refinement with a stationary grid is also feasible.

The scattered beam grid 4 should in this case be designed such that it can be inserted into a conventional grid drawer, so that on the one hand it is possible to make use of already known guide elements or inserts for the grid drawer, while on the other hand it is possible to retrofit already existing apparatuses according to an embodiment of the invention. The radiation receiver 5 remains in its original position within the apparatus or within the apparatus frame.

As an alternative to this, it is feasible not to change the position of the scattered beam grid 4, as is done by the scattered beam grid used in conventional apparatuses, but in contrast to rotate the radiation receiver 5. This can be done in a simple way by the capability to rotate the radiation receiver itself about an axis at right angles to the plane of the scattered beam grid.

As an alternative to the described embodiment of the radiation detector as a solid-state image detector, it is also possible to use a storage film as the radiation detector 5. This is exposed to radiation, and charges are also generated locally there. However, the reading process does not make use of receiver-end reading electronics, but of a separate reading device, to which the storage film must be passed after the image has been recorded. It would, of course, also be feasible to integrate a reading device such as this in the apparatus.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An apparatus for radiation image recording, comprising:
   a radiation receiver adapted to receive radiation and convert incident radiation to an electrical charge which represents a measure of the incident radiation and which is readable line-by-line via a reading device; and
   a scattered beam grid, associated with the radiation receiver and including absorption elements which run in straight lines, with the absorption elements being at an angle to the line-by-line reading direction, wherein the scattered beam grid is rotated with respect to the radiation receiver, and wherein the grid is designed to be insertable into a conventional grid drawer, wherein the inserted position is rotated with respect to the radiation receiver.

2. The apparatus as claimed in claim 1, wherein the angle is $\geq 5°$ and $\leq 90°$.

3. The apparatus as claimed in claim 1, wherein the grid is movable with respect to the radiation receiver.

4. The apparatus as claimed in claim 1, wherein at least one of the scattered beam grid, accommodated in a grid draw, is rotatable, and the grid drawer is rotatable with respect to the radiation receiver.

5. The apparatus as claimed in claim 1, wherein the radiation receiver is at least one of a digital solid state detector and a storage film.

6. The apparatus as claimed in claim 2, wherein the grid is movable with respect to the radiation receiver.

7. The apparatus as claimed in claim 2, wherein at least one of the scattered beam grid, accommodated in a grid draw, is rotatable, and the grid drawer is rotatable with respect to the radiation receiver.

8. The apparatus as claimed in claim 2, wherein the radiation receiver is at least one of a digital solid state detector and a storage film.

9. The apparatus as claimed in claim 3, wherein at least one of the scattered beam grid, accommodated in a grid draw, is rotatable, and the grid drawer is rotatable with respect to the radiation receiver.

10. The apparatus as claimed in claim 3, wherein the radiation receiver is at least one of a digital solid state detector and a storage film.

11. The apparatus as claimed in claim 1, wherein at least one of the scattered beam grid, accommodated in a grid draw, is rotatable, and the grid drawer is rotatable with respect to the radiation receiver.

12. The apparatus as claimed in claim 4, wherein the radiation receiver is at least one of a digital solid state detector and a storage film.

13. An apparatus for radiation image recording, comprising:

means for receiving converting received incident radiation to an electrical charge representing a measure of the incident radiation, readable line-by-line via a reading device; and a scattered beam grid, associated with the means for receiving and including absorption elements which run in straight lines, with the absorption elements being at an angle to the line-by-line reading direction, wherein the scattered beam grid is rotated with respect to the means for receiving, and wherein the grid is designed to be insertable into a conventional grid drawer, wherein the inserted position is rotated with respect to the means for receiving.

14. The apparatus as claimed in claim 13, wherein the angle is $\geqq 5°$ and $\leqq 90°$.

15. The apparatus as claimed in claim 13, wherein the grid is movable with respect to the means for receiving.

16. The apparatus as claimed in claim 13, wherein at least one of the scattered beam grid, accommodated in a grid draw, is rotatable, and the grid drawer is rotatable with respect to the r means for receiving.

17. The apparatus as claimed in claim 13, wherein the means for receiving includes at least one of a digital solid state detector and a storage film.

18. The apparatus as claimed in claim 14, wherein the grid is movable with respect to the means for receiving.

* * * * *